United States Patent [19]

King

[11] 4,448,998

[45] May 15, 1984

[54] CATALYTIC HYDROGENATION OF N,N-DISUBSTITUTED AMIDES TO AMINES

[75] Inventor: Richard M. King, Cincinnati, Ohio

[73] Assignee: The Procter & Gamble Company, Cincinnati, Ohio

[21] Appl. No.: 443,426

[22] Filed: Nov. 22, 1982

[51] Int. Cl.³ .............................................. C07C 85/12
[52] U.S. Cl. .................................... 564/488; 564/420; 502/60; 502/78; 502/79
[58] Field of Search .............................. 564/488, 420; 252/455 Z

[56] References Cited

U.S. PATENT DOCUMENTS 3,190,922  6/1965  Le Bard et al. ...................... 260/583
3,444,204  5/1969  Schutt ................................... 260/583

FOREIGN PATENT DOCUMENTS 1493839  5/1970  German Democratic Rep. ..................................... 564/488

OTHER PUBLICATIONS

J. Am. Chem. Soc., vol. 56, pp. 2419–2424, 1934, Wojcik et al., "Catalytic Hydrogenation of Amides to Amines."

Primary Examiner—Paul F. Shaver
Attorney, Agent, or Firm—Richard C. Witte; Ronald L. Hemingway

[57] ABSTRACT

N,N-disubstituted amides are hydrogenated to tertiary amines in the presence of a catalyst system comprising copper chromite and zeolite.

12 Claims, No Drawings

CATALYTIC HYDROGENATION OF N,N-DISUBSTITUTED AMIDES TO AMINES

FIELD OF THE INVENTION

The invention pertains to the preparation of tertiary amines from the N,N-disubstituted amides of carboxylic acids by the catalytic hydrogenation of the amides.

BACKGROUND ART

The hydrogenation of N,N-disubstituted amides to amines in the presence of a copper chromite catalyst is known to the art. See U.S. Pat. Nos. 3,190,922, Bard et al., issued June 22, 1965, and 3,444,204, Schutt, issued May 13, 1969, and Wojcik et al., *J. Am. Chem. Soc.*, 56:2419 (1934). In general, these processes are characterized by relatively long reaction times when conducted in batch reactors or relatively long residence times in the reactor when conducted in a continuous manner, especially when the reaction is conducted under relatively mild conditions of temperature and pressure, e.g., 140 kg./sq.cm. pressure and 260° C.

SUMMARY OF THE INVENTION

The present invention is directed to an improved catalytic process for hydrogenation of N,N-disubstituted amides of carboxylic acids to produce tertiary amines. The improvement resides in the use of catalyst system comprising copper chromite and zeolite.

DETAILED DESCRIPTION OF THE INVENTION

In accordance with the present invention it has been found that improvements (particularly in speed of reaction) in the copper chromite-catalyzed hydrogenation of N,N-disubstituted alkyl carboxylic acid amides to tertiary amines can be obtained by using a dual catalyst system of copper chromite and zeolite.

Accordingly, the present invention comprises a process for producing tertiary amines by hydrogenation of N,N-disubstituted amides of carboxylic acids, the said process being conducted with gaseous hydrogen at a temperature of from about 200° C. to about 400° C. and a pressure of from about 140 to about 350 kg/sq.cm., and in the presence of a catalyst composition comprising copper chromite and zeolite, the weight ratio of copper chromite:zeolite being from about 10:1 to about 0.1:1. All percentages and ratios herein are "by weight" unless specified otherwise.

The present invention also comprises the novel catalyst system.

The process of the present invention is generally useful in hydrogenating any N,N-disubstituted amide group to the corresponding amine. The process is particularly useful in preparing amines having 10 to 72 carbon atoms from amides having the same number of carbon atoms, although even higher molecular weight materials can be prepared. Similarly, the process can be used to prepare lower molecular weight amines; however, these amines are generally more economically prepared by other routes. Thus, the process is most especially useful in preparing tertiary amines in which one or more of the radicals attached to the nitrogen atom is a higher aliphatic radical of 8–24 carbon atoms. Representative amides which are useful in preparing these tertiary amines have the formula:

wherein R, R', and R" are hydrocarbon radicals of 1 to 24 carbon atoms and where at least one of R, R', or R" has 8–24 carbon atoms. In addition R' and R" can be part of a cyclic ring. Preferably the hydrocarbon radicals are aliphatic and most preferably R is an alkyl radical of from 8 to 18 carbon atoms and R' and R" are alkyl radicals of 1 to 3 carbon atoms.

Another group of particularly useful starting materials are those disubstituted amides prepared from dibasic acids. These compounds, of course, contain two amide groups. Upon hydrogenation, both amide groups are converted to amine groups. Adipic acid and dimerized linoleic acid are particularly useful in preparing suitable amide starting materials. Similarly, if a starting material is employed which contains three or more disubstituted amide groups, each amide group will be hydrogenated.

Specific examples of compounds useful as starting materials include N,N-dimethylstearamide; N,N-dimethylpalmitamide; N,N-dimethyllauramide; N,N-dimethylcocoamide; N,N-dimethyloleamide; N,N,N',N'-tetramethyladipamide; N,N,N',N'-tetra-n-octyladipamide; N,N-distearylstearamide; N,N-dibutylpalmitamide; N,N-dicyclohexylstearamide; N,N-di-2-ethylhexylmyristamide; N,N-di-n-dodecylisooctanamide, N,N,N',N'-tetramethyl amide of dimerized linoleic acid, N,N,N',N'-tetra(2-ethylhexyl)amide of dimerized linoleic acid; N,N'-di-tetradecylpiperazine.

The copper chromite catalyst used in the present invention is well known in the hydrogenation art. It is also referred to in the art as copper-chromium oxide catalyst. Its preparation is discussed in an article by Connor, Folkers and Adkins in the *Journal of the American Chemical Society*, vol. 54, pp. 1138–45 (1932), and in "Reactions of Hydrogen With Organic Compounds Over Copper-Chromium Oxide and Nickel Catalysts," by Homer Adkins, University of Wisconsin Press, Madison, Wisc. (1937). The nature of this catalyst is further discussed in an article by Adkins, Burgoyne, and Schneider in the *Journal of the American Chemical Society*, vol. 72, pp. 2626–29 (1950). Many types of copper-chromium oxide hydrogenation catalysts are commercially available and are generally useful in the instant invention. It is preferred to use a catalyst containing 40% to 65% CuO (assuming all copper is present as CuO) and 35% to 60% $Cr_2O_3$ (assuming all chromium to be present as $Cr_2O_3$). Some commercially available copper-chromium oxide catalysts contain small amounts of catalyst stabilizers, e.g., barium oxide. While these stabilizers apparently do not improve the catalyst from the standpoint of this reaction, catalysts containing such stabilizers can be employed if desired.

The co-catalysts which are used with copper chromite in the present invention are the crystalline aluminosilicate materials known as zeolites. The zeolites occur naturally or can be produced synthetically, and are available from commercial sources such as Linde Company, Tonawanda, N.Y. Examples of naturally occurring zeolites are faujasite, chabazite and mordenite. Examples of synthetic zeolites are Zeolite A, Zeolite X and Zeolite Y. Specific types of zeolites can have different pore sizes, depending on the cation present in the structure. The approximate pore size (in Angstroms) is usually indicated by a number preceding the letter identifying the zeolite, e.g., Zeolite 4A, Zeolite 10X, and Zeolite 13X, indicating approximate pore sizes of 4, 10, and 13 Angstroms, respectively. Both natural and synthetic zeolites can be used in the present invention.

In the catalyst system of the invention, the weight ratio of copper chromite to zeolite should be in the range of from about 10:1 to about 0.1:1, preferably from about 1:1 to about 0.2:1, and most preferably from about 0.5:1 to about 0.3:1. The catalyst should preferably have a particle size within the range of from about 1 to about 50 microns.

The amount of catalyst employed in the process is not critical. A greater amount of catalyst generally increases somewhat the rate of reaction, but does not affect the nature of the final product. Catalyst usage in amounts of 1% to 25% of the combined catalyst based on weight of amide is generally sufficient.

The reaction temperature should be in the range of from about 200° C. to about 400° C., preferably from about 260° C. to about 310° C.

It is desirable to maintain a hydrogen pressure of from about 140 kg./sq.cm. to about 350 kg./sq.cm Pressures above 350 kg./sq.cm. can be used but no particular advantage exists for such high pressures. Most preferably the reaction pressure should be maintained in the range of 200 kg./sq.cm. to about 250 kg./sq.cm.

The reaction can be carried out as a batch or continuous process.

The invention will be illustrated by the following example, which demonstrates the improvement in catalytic activity obtained by using the mixed catalyst system of the present invention compared to using copper chromite alone.

EXAMPLE I

Reduction of Amide With and Without Zeolite Co-Catalyst

N,N-dimethyllauramide (17.0 g, 0.075 mole) and copper chromite catalyst (0.51 g, 3.0 wt. % based on amide) were charged into a pyrex autoclave liner fitted with a thermocouple well. In Run I powdered zeolite molecular sieve (Linde 4A, 3.00 g, 18 wt. % based on amide) was added to the reaction mixture; in Run II the zeolite was omitted. In each run the pyrex liner was sealed in a steel bomb and the mixture was hydrogenated in a rocking autoclave under the following conditions: 140 kg./sq.cm. H$_2$ pressure, 287° C., 60 minutes reaction time. Agitation (rocking) was at about 50 cycles per minute. At the end of the reaction time, hydrogen was vented to about 35 kg./sq.cm., the bomb was cooled to about 90° C., and the product mixture was removed, filtered, and analyzed by gas chromatography. The results, tabulated below, show that zeolite substantially improves both conversion and selectivity for production of alkyldimethylamine in this reaction.

TABLE 1

|  | Run I | Run II |
|---|---|---|
| Zeolite 4A (Wt. %) | (18) | None |
| Unreacted Amide (Wt. %) | 8.4 | 53.4 |
| Alkyldimethylamine (Wt. %) | 72.4 | 16.5 |
| Dialkylmethylamine (Wt. %) | 9.2 | 8.6 |
| Lauryl Alcohol (Wt. %) | 8.3 | 1.1 |
| Unknown (Wt. %) | Nil | 9.4 |
| % Conversion | 91.6 | 46.6 |
| % Selectivity | 80.5 | 46.3 |

What is claimed is:

1. A process for producing tertiary amines containing from about 10 to about 72 carbon atoms by hydrogenation of the corresponding N,N-disubstituted amides, the said process being conducted with gaseous hydrogen at a temperature of from about 200° C. to about 400° C. and a pressure of from about 140 to about 350 kg./sq.cm., and in the presence of a catalyst composition comprising copper chromite and zeolite, the weight ratio of copper chromite:zeolite being from about 10:1 to about 0.1:1.

2. The process of claim 1 wherein the amides have the formula

wherein R, R', and R" are hydrocarbon radicals of from 1 to 24 carbon atoms.

3. The process of claim 2 wherein the weight ratio of copper chromite:zeolite is from about 1:1 to about 0.2:1.

4. The process of claim 3 wherein R, R' and R" are aliphatic radicals.

5. The process of claim 4 wherein the zeolite in the catalyst composition is selected from the group consisting of Zeolite A, Zeolite X, Zeolite Y, faujasite, chabazite and mordenite.

6. The process of claim 5 wherein the temperature is from about 260° C. to about 310° C. and the pressure is from about 140 to about 250 kg./sq.cm.

7. The process of claim 6 wherein the zeolite is Zeolite 4A and the amide is N,N-dimethyllauramide.

8. A novel catalyst composition comprising a mixture of copper chromite and zeolite in a weight ratio of said copper chromite to said zeolite of from about 10:1 to about 0.1:1.

9. The composition of claim 8 wherein the weight ratio is from about 1:1 to about 0.2:1.

10. The composition of claim 9 wherein the zeolite is selected from the group consisting of Zeolite A, Zeolite X, Zeolite Y, faujasite, chabazite and mordenite.

11. The composition of claim 10 wherein the zeolite is Zeolite A.

12. The composition of claim 11 wherein the zeolite is Zeolite 4A.

* * * * *